United States Patent
Welch et al.

(10) Patent No.: US 7,258,868 B2
(45) Date of Patent: *Aug. 21, 2007

(54) VOLATILE RELEASING SUBSTRATES AND METHODS FOR PREPARING THEM

(75) Inventors: Kenneth J. Welch, Racine, WI (US); Robert R. Emmrich, Racine, WI (US); Michael J. Aulozzi, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 591 days.

This patent is subject to a terminal disclaimer.

(21) Appl. No.: 10/758,650

(22) Filed: Jan. 15, 2004

(65) Prior Publication Data

US 2005/0158353 A1    Jul. 21, 2005

(51) Int. Cl.
*A01N 25/08*    (2006.01)
*A01N 65/00*    (2006.01)

(52) U.S. Cl. .................... 424/409; 424/441; 424/417; 424/421; 514/65; 514/521; 514/522; 514/531

(58) Field of Classification Search ............... 514/521, 514/522, 531; 424/409, 417, 421
See application file for complete search history.

(56) References Cited

U.S. PATENT DOCUMENTS

| | | | |
|---|---|---|---|
| 3,288,615 A | 11/1966 | Estes et al. | |
| 3,995,595 A | * 12/1976 | Williams | ............... 119/61.53 |
| 4,421,477 A | 12/1983 | Adachi et al. | |
| 4,663,315 A | 5/1987 | Hasegawa et al. | |
| 4,874,516 A | 10/1989 | Kondo | |
| 4,968,487 A | 11/1990 | Yamamoto et al. | |
| 5,038,394 A | 8/1991 | Hasegawa et al. | |
| 5,290,546 A | 3/1994 | Hasegawa et al. | |
| 5,547,616 A | 8/1996 | Dancs et al. | |
| 6,031,967 A | 2/2000 | Flashinski et al. | |
| 6,309,986 B1 | 10/2001 | Flashinski et al. | |

FOREIGN PATENT DOCUMENTS

| | | | |
|---|---|---|---|
| EP | 0253640 | * | 1/1988 |
| WO | WO 00/781335 A2 | | 12/2000 |
| WO | 2004068945 A1 | | 8/2004 |
| WO | WO2004/068945 | * | 8/2004 |

OTHER PUBLICATIONS

Reeder D H, et al.: "Models for Polybutadiene Pore Wall Coatings in Porous Zirconia" Journal of Chromatography A, Elsevier, Amsterdam, NL, vol. 760, No. 1, Jan. 24, 1997, pp. 71-79, XP004054902 ISSN: 0021-9673 p. 71 through p. 73.

* cited by examiner

*Primary Examiner*—Neil S. Levy (57) ABSTRACT

Substrates are provided for use in a heating and/or blowing device that dispenses volatile material. The substrates are a porous medium (such as porous ceramic) having their interior pores coated by a polymeric material (such as a polysiloxane). The substrate is impregnated with a volatile such as pyrethrum. The substrate is less susceptible to clogging. Also disclosed are methods of making those substrates in which the polymeric material is wicked into the substrate with a volatile solvent.

15 Claims, 8 Drawing Sheets

VOLATILE RELEASING SUBSTRATES AND METHODS FOR PREPARING THEM

CROSS-REFERENCE TO RELATED APPLICATIONS

Not applicable

STATEMENT REGARDING FEDERALLY SPONSORED RESEARCH/DEVELOPMENT

Not applicable

BACKGROUND OF THE INVENTION

The present invention relates to devices, especially heating devices, that dispense volatiles from a substrate such as a wick, mat or plug. More particularly, the invention relates to ways to reduce the tendency of such substrates to clog during dispensing.

A variety of devices for dispensing volatilizable materials are well known. Such volatilizable materials may be air scents or deodorizers (e.g. fragrances or masks), pest control materials (e.g., insecticides, insect repellants or insect growth control regulators), allergen control ingredients, disinfectants, or other materials.

In some of these devices a wick (typically an essentially cylindrical wick) is provided which draws volatile from a reservoir to a dispensing area. An upper/outer end of the wick is heated. See e.g. U.S. Pat. No. 4,663,315. The disclosure of this patent and of all other publications referred to herein are incorporated herein by reference as if fully set forth herein.

In other such devices a porous mat is impregnated with a volatile material. These impregnated mats are placed on heating plates to cause the volatile material to vaporize. Examples of this type of mat are provided in U.S. Pat. No. 6,309,986. An example of an electric heater suitable to cause such mats to dispense volatiles is disclosed in U.S. Pat. No. 6,031,967.

In still other types of such devices a porous mat that has been impregnated with a volatile material is held within a device such that a flow of hot gases from a fuel burner (such as a candle) passes by the mat and thereby causes the volatile material to vaporize. An example of this type of device is disclosed in WO 00/78135.

In yet another type of such a dispensing device, moving air is directed against or through a substrate to thereby volatilize material that the substrate has been impregnated with. An example of this type of device is disclosed in U.S. Pat. No. 5,547,616.

Our assignee recently filed a patent application on Jan. 30, 2003 with U.S. Ser. No. 10/354,876. That application covered various improvements in wick, mat and plug structures used to dispense volatile materials. That application disclosed providing an array of granular particles (e.g. sand) coated with a binder (e.g. a thermoset polymeric material) structured to form a network of pores in the wick, with the wick being impregnated with a variety of volatiles. While this device was an improvement for many volatiles, it was not optimal for use with certain others of interest (e.g. those containing pyrethrum, a desirable insecticide).

In this regard, many dispensing devices which rely on heat to dispense actives from wicks, mats or plugs can experience clogging problems for certain volatiles. This can be due to the breakdown of the volatile when heated, or due to reactions or binding that occurs involving the volatile when heated. When such clogging occurs, the release rate of the volatile becomes non-uniform, and may in some cases prematurely stop entirely, thus wasting the remaining active trapped in the substrate. Even where some release continues, the release may be at such a low level that the device is not effective for its designed purpose.

For example, pyrethrum insecticide tends to form non-volatile waxes or polymers upon heating which clog wicks, mats and plugs. Similar problems arise with materials containing terpenes.

One proposed solution to this problem has been to use antioxidants in the impregnation liquid. See e.g. U.S. Pat. No. 4,968,487. However, this can add cost to the formulation, and only has some effect when oxidation is central to the clogging issue. Moreover, in spite of the inclusion of antioxidants, some cross-linking of the isoprene units in certain liquid formulations can occur, ultimately leading to the clogging of the wick, mat or plug anyway. This is particularly a problem for wicks intended for providing long term insecticidal protection.

Thus, there is a need for an improved dispensing substrate that can be used in such dispensing devices with reduced clogging tendency.

BRIEF SUMMARY OF THE INVENTION

In one aspect the invention provides a substrate impregnated with a volatile material to be dispensed. The substrate has been formed from a medium having pores and passages, where the medium has a polymeric material coating interior surfaces of the pores and passages. There is a volatile material disposed in the pores which is selected so that the volatile material is more volatile than the polymeric material. The polymeric material inhibits the volatile material from clogging the substrate if the substrate is heated.

In preferred forms the polymeric material is a polysiloxane, especially polyalkylsiloxanes and polyalkylarylsiloxanes where the alkyl group has less than ten carbons. In the most preferred forms the polysiloxane is selected from the group consisting of polydimethylsiloxane, polymethylphenylsiloxane, and polymethyloctylsiloxane, in each case with the polysiloxane having a molecular weight of 750 dalton or greater.

Alternatively other polymeric materials can be used such as phenol formaldehyde, polyurethane, and fluorocarbon polymers like polytetrafluoroethylene and polydifluoroethylene. In any event, preferably the polymeric material is between about 0.2% to about 4% (e.g. about 1%) of the substrate by weight.

In the most preferred forms, the substrate is capable of being heated at 200° C. so as to release at least 90 or 95 percent of the volatile material from the substrate, the substrate is selected from the group consisting of wicks, mats and plugs, and the medium is selected from the group consisting of ceramics, sand, sawdust, cellulosic materials and metals. It is desirable that the substrate is designed so that if heated to 200° C. for 24 hours the polymeric material therein will not have decomposed as a result thereof.

The volatile material may be selected from a wide variety of formulations. See e.g. U.S. Pat. No. 6,309,986 for a disclosure of many insect control materials, deodorizers, fragrances and disinfectants known to be suitable for use with heating dispensers. Typically there will be at least one hydrocarbon solvent having a high boiling point (as a carrier), one or more actives (e.g. an insecticide), and optionally an antioxidant and a fragrance. The formulation will be tailored for the application, and may have a variety of different ingredients as is conventional for the application. We prefer to use the invention with insecticidal formulations having a combination of pyrethrum and a synthetic insecticide, together with a fragrance (orange oil), isoparaffinic solvents, and an antioxidant (BHT).

Without intending to be limited by theory, the inventors believe that the polymeric material transforms the interior surface of the substrate from a relatively high contact angle surface to a relatively low contact angle surface for the volatile material that the substrate is employed to transport and dispend. A wick is a series of short intersection capillary segment. A lower contact angle provides better wetting and higher capillarity (higher surface energy).

Figure 12A:
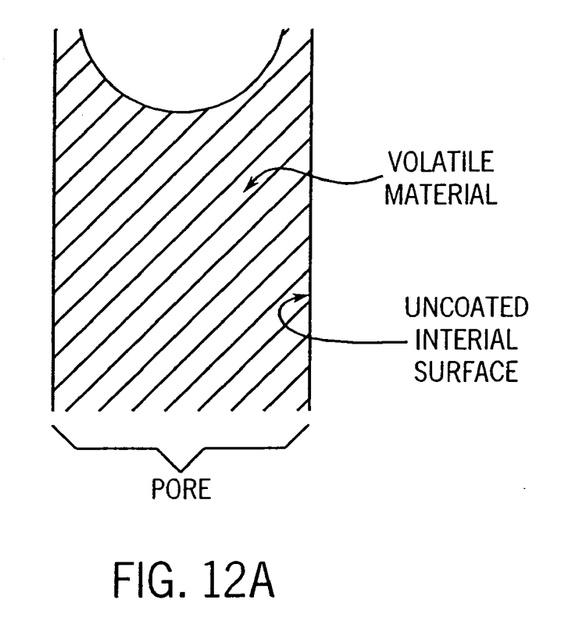
FIGS. 12A and 12B depict the effect of polymer coating on volatile material distribution in pores and passages of a substrate of the present invention.
Figure 12B:
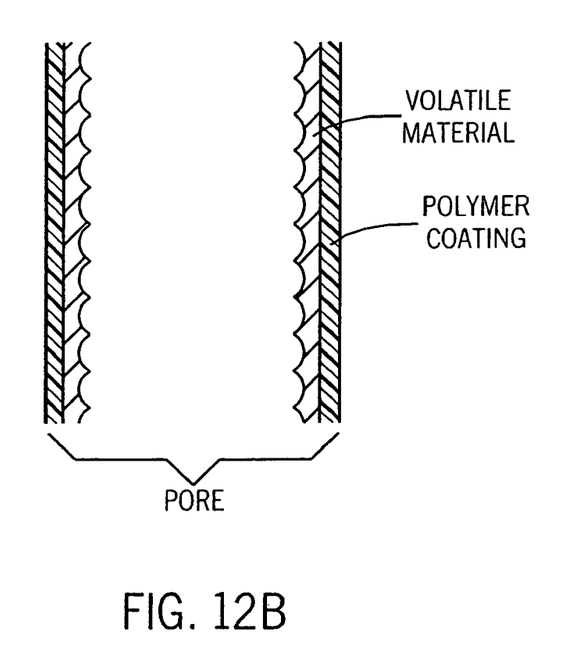

Many volatile materials such as pyrethrum are susceptible to free radical polymerization. In an uncoated wick with a relatively high contact angle, the volatile material will fill the entire pore (see FIG. 12A). When the polymerization is initiated, it occurs across the opening of the core, leading to the clogging of the wick. In a wick that is coated with a polymeric material of the present invention, the volatile material lays flat against the pore surface and thus any polymerization that occurs will proceed along the surface of the pore rather than across the opening of the pore (see FIG. 12B). Accordingly, the polymerization events are less likely to clog the wick. Furthermore, the polymeric coating masks the active polymerization sites in a mineral substrate and thus can reduce the polymerization events from occurring in the first place.

In another aspect the invention provides a method for forming a substrate of the above kind. One provides the porous medium, dissolves the polymeric material in a volatile solvent to form a solution, and allows the solution to wick into (or otherwise impregnate) the pores and passages. One then permits the substrate to expel at least a portion of (preferably essentially all) the volatile solvent from the substrate, preferably facilitated by heating the substrate, or exposing it to negative pressure, or passing gas over its surface, or by a combination of these techniques.

Preferred solvents for this purpose are selected from the group consisting of chloroform, tetrahydrofuran, dioxane, methylene chloride, acetone, supercritical carbon dioxide and dimethylsulfoxide. Their most desirable feature is the ability to dissolve the polymeric material for wicking purposes, while being able to be readily removed from the substrate thereafter.

Alternatively, to form a substrate of the present invention, resin beads of a suitable polymeric material can be mixed with a material for forming the porous medium. The mixture is subject to the conventional processes for forming a porous medium, which can be readily achieved by a skilled artisan. The substrate so formed will have pores and passages the surfaces of which are coated by the polymeric material.

It will be appreciated from the discussions above and below that the present invention provides a way of coating the internal pores of a ceramic wick, mat or plug with a material that helps the substrate avoid clogging. Polysiloxanes are particularly preferred. They are heat-resistant so that they do not cause a separate clogging problem, and they do not emit undesirable odors.

The invention is particularly advantageous in reducing the waste of actives by permitting the substrate to release essentially all active within it. Further, it provides substrates that release actives in a more uniform and predictable manner.

These and still other advantages of the present invention will be apparent from the description which follows and the accompanying drawings. In them reference is made to certain preferred embodiments. However, the claims should be looked to in order to judge the full scope of the invention, and the claims are not to be limited to just the preferred embodiments.

DETAILED DESCRIPTION OF THE PREFERRED EMBODIMENT

Figure 1A:
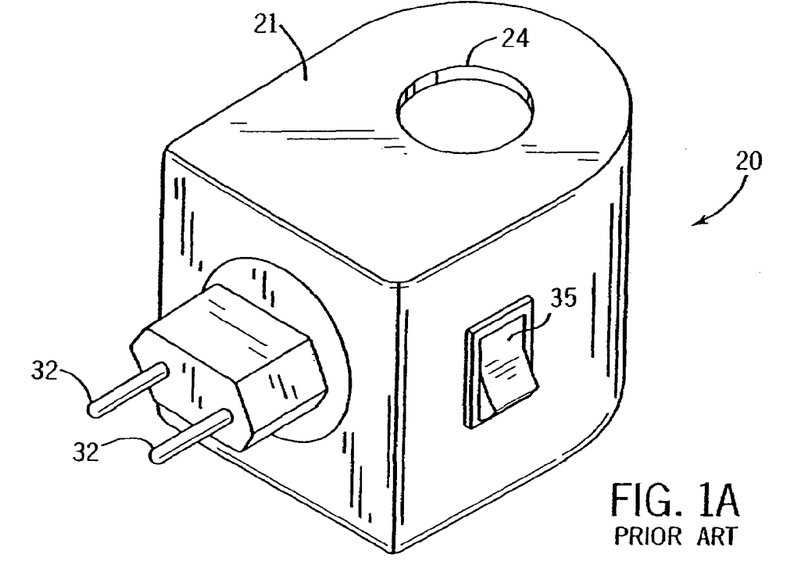
FIG. 1A is a perspective view showing a prior art device for dispensing volatile materials.
Figure 1B:
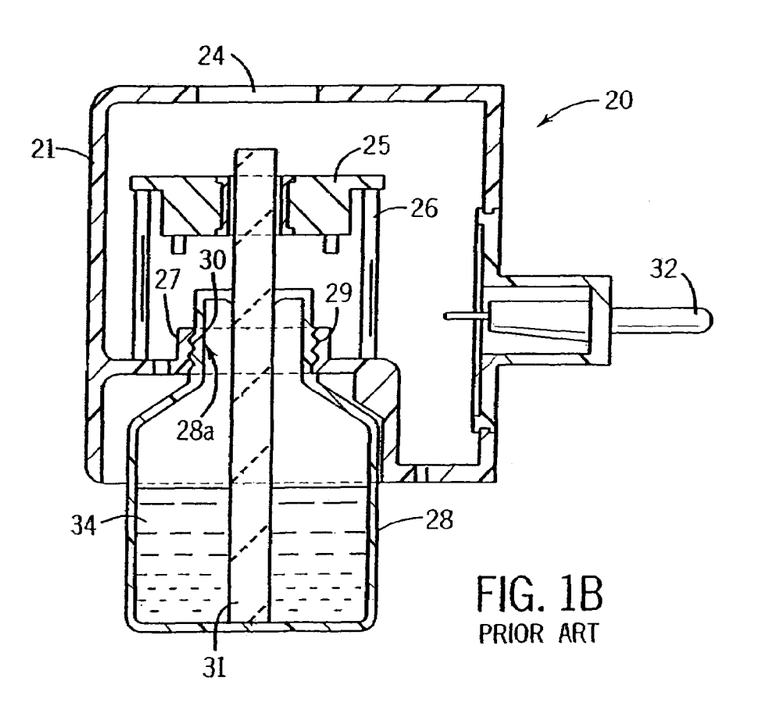
FIG. 1B is a vertical cross-sectional view of the FIG. 1A device.

Referring first to FIGS. 1A and 1B, there is shown a prior art dispensing device 20 in which a heat source is used to promote the wicking action and release of a volatile material from a wick immersed in a volatile liquid contained in a reservoir. The dispensing device 20 includes a body 21 having a vapor outlet 24 formed in the center of the top of the body 21. A ring heater 25 having an opening extending vertically there through is provided inside the body 21 below the vapor outlet 24. The ring heater 25 is supported by a stay 26. Provided under the heater 25 is a bottle socket 27 having an opening extending vertically there through. The socket 27 is formed on its inner periphery with a threaded portion 30 adapted for threaded engagement with a threaded portion 29 on the outer periphery of the mouth 28a of a volatile liquid bottle 28.

The bottle 28 is provided with a wick 31 that is insertable into the ring heater 25 concentrically therewith when the bottle 28 is threaded at its mouth 28a into the socket 27. The wick 31 is immersed in the liquid 34 in the bottle 28 and upwardly transports the liquid 34 contained in the bottle 28 by capillary action. The wick 31 is typically formed from a fired porous ceramic or a sintered plastic material.

Electrical plug blades 32 are fixed to the body 21 on its rear side. The plug blades 32 are connected to the ring heater 25 in a conventional manner. The ring heater 25 is energized by inserting the plug blades 32 into an electrical outlet and activating switch 35, whereby the ring heater 25 produces heat to heat the upper portion of the wick 31. The heat usually promotes upward transport of the liquid 34 in the wick 31. The liquid chemical 34 in the wick 31 is vaporized by the heat from the ring heater 25. A more detailed description of this type of device can be found in U.S. Pat. No. 5,290,546.

It should be appreciated that a wick of the present invention could be shaped in the same shape as wick 31. If this were done, the revised wick could be used in the FIG. 1B device as shown.

Figure 2:
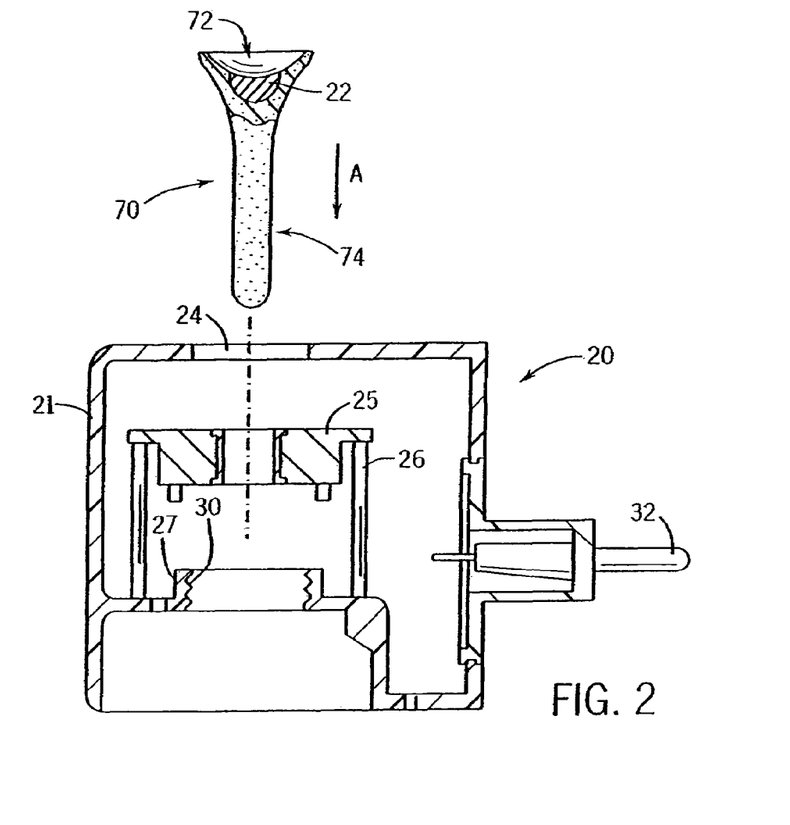
FIG. 2 is a vertical cross-sectional view of a portion of the FIG. 1B device, but with a wick of the present invention about to be inserted therein.
Figure 3:
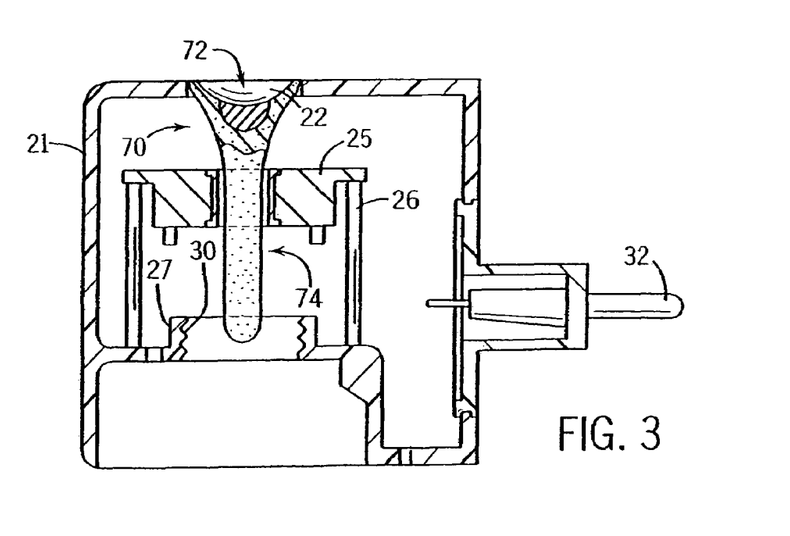
FIG. 3 is a view similar to FIG. 2, but with the wick fully inserted.

Turning now to FIGS. 2 and 3 such a device can be used with a revised wick/plug 70. The plug shown in FIG. 2 can be made from a standard wick ceramic substrate (e.g., from Rauschert or CeramTec), which is a ceramic made of alumina. Such a wick can then be coated with a polysiloxane in accordance with the present invention. The resulting substrate can then be used to wick a solution containing natural pyrethrum in a hydrocarbon solvent.

The plug 70 has a truncated cone shaped head 72 and a cylindrical body 74 that extends downwardly from the head 72. The body 74 of the plug 70 is made small enough to be inserted from above into the hole 24 of the dispensing device 20, while the head 72 is made too wide to slip through the hole 24. The body 74 of the plug 70 is also made small enough to be insertable into the ring heater 25 concentrically therewith as shown in FIG. 3. The head 72 at the top of the plug 70 is useful for handling.

The porous plug 70 is inserted into the dispensing device 20 by moving the plug 70 in the direction "A" shown in FIG. 2 (in this orientation downward). The ring heater 25 is then energized by inserting the plug blades 32 into an electrical outlet and activating switch 35, whereby the ring heater 25 produces heat to heat the body 74 of the plug 70. The volatile material 22 in the plug 70 is vaporized by the heat from the ring heater 25 and enters the surrounding atmosphere.

Figure 4A:
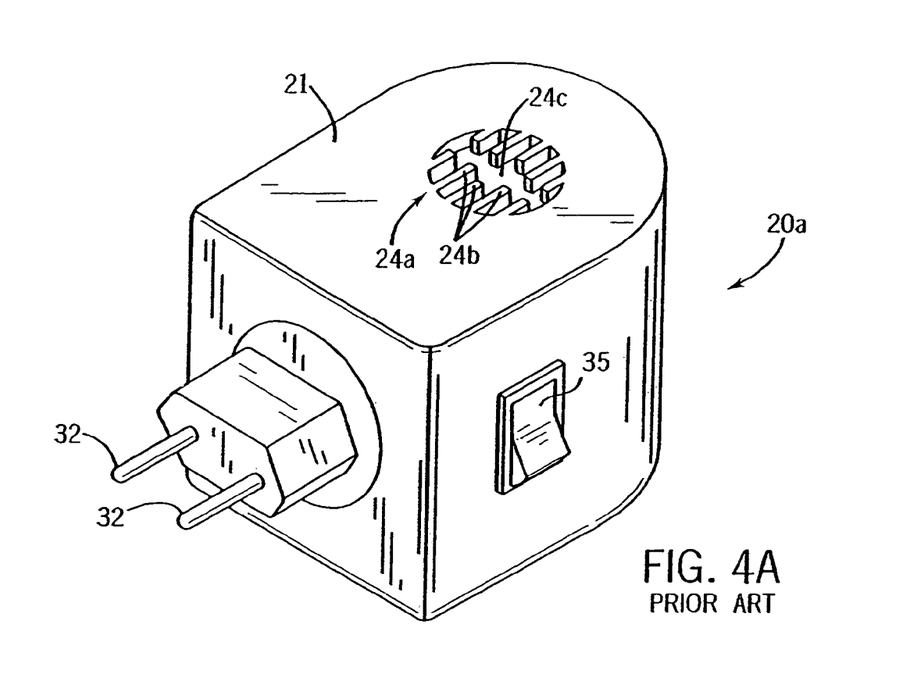
FIG. 4A is a view similar to FIG. 1A, but with an outlet portion slightly modified.
Figure 4B:
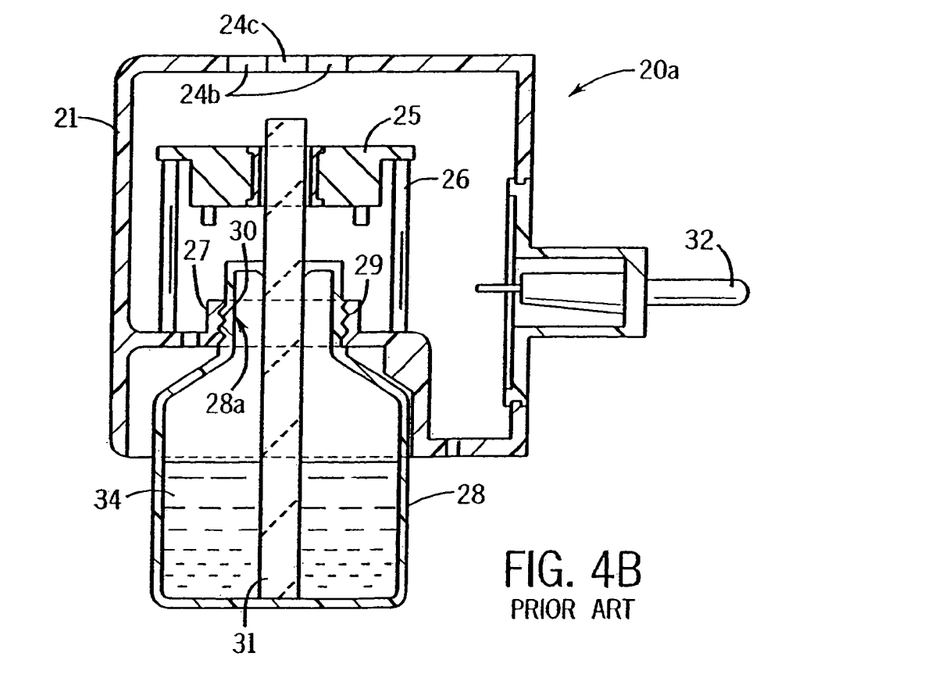
FIG. 4B is a view similar to FIG. 1B, but of the FIG. 4A embodiment.

Referring next to FIGS. 4A and 4B, there is shown another prior art heated volatile dispensing device 20a. This is similar to the FIG. 1A device but for having a different vapor outlet 24a formed in the center of the top of the body 21. The vapor outlet 24a includes inwardly projecting fingers 24b which define a generally rectangular opening 24c.

Figure 5:
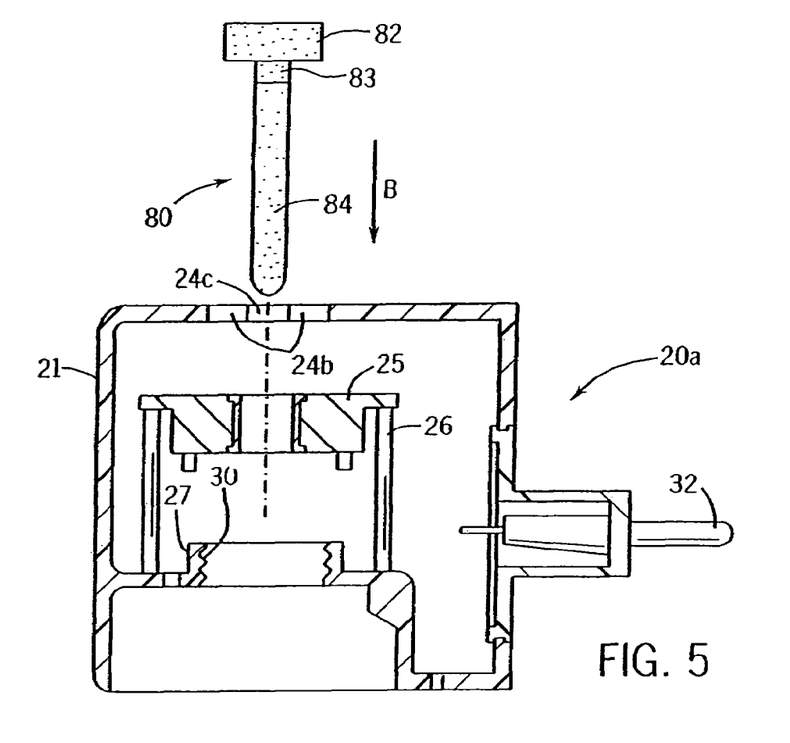
FIG. 5 is a view similar to FIG. 2 but with the device apart from the wick being of the FIG. 4A type, and the wick being a modified wick of the present invention.
Figure 6:
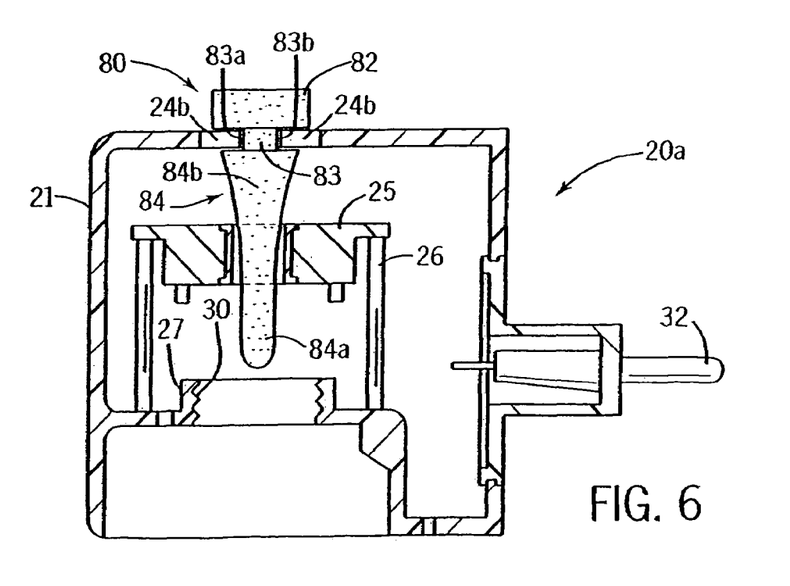
FIG. 6 is a view similar to FIG. 3 but with a different embodiment of a wick of the present invention.

FIGS. 5 and 6 are similar to FIGS. 2 and 3 but for the different wicks and the slight difference in the upper opening 24a-c. Here a porous plug or peg 80 according to the invention is impregnated with a volatile material. The porous plug 80 includes a disk shaped head 82 and a body 84 that extends downwardly from the head 82. The body 84 of the plug 80 is shown in a side view in FIG. 5. It can be seen that in a side view, the perimeter of the body 84 of the plug 80 has an essentially rectangular shape.

The body 84 of the plug 80 is shown in a front view in FIG. 6. It can be seen that in a front view, the body 84 of the plug 80 includes a lower section 84a having an essentially rectangular perimeter, a middle section 84b having an essentially V-shaped perimeter, and an upper section 83 that extends from the middle section 84b to the head 82. With the plug 84 oriented as shown in FIG. 5, the body 84 of the plug 80 is narrow enough to be inserted from above into the rectangular opening 24c of the dispensing device 20a, while the head 82 is made too wide to slip through the rectangular opening 24c. The body 84 of the plug 80 is also made small enough to be insertable into the ring heater 25 concentrically therewith as shown in FIG. 6.

The porous plug 80 is inserted into the dispensing device 20a by moving the plug 80 in the direction "B" shown in FIG. 5 (downward in this orientation). The porous plug 80 may then be rotated 90 degrees into a position as shown in FIG. 6. When the plug 80 is in this position, the inwardly projecting fingers 24b of the vapor outlet 24a are positioned in grooves 83a and 83b between the middle section 84b and the head 82 of the plug 80. The plug 80 is thereby secured in the dispensing device 20a until the plug is rotated 90 and lifted up and out of the dispensing device 20a. Thus, the squared-off shank section of the shape shown fits into the existing, rectangular opening 24c in the top of the heater, entering only when turned to the correct position.

Once in place, the plug can be turned, preventing its removal until turned again to its original position. After the plug 80 is inserted, the ring heater 25 is then energized by inserting the plug blades 32 into an electrical outlet and activating switch 35 whereby the ring heater 25 produces heat to heat the body 84 of the plug 80. The volatile material in the plug 80 is then vaporized by the heat from the ring heater 25 and enters the surrounding atmosphere.

Figure 7:
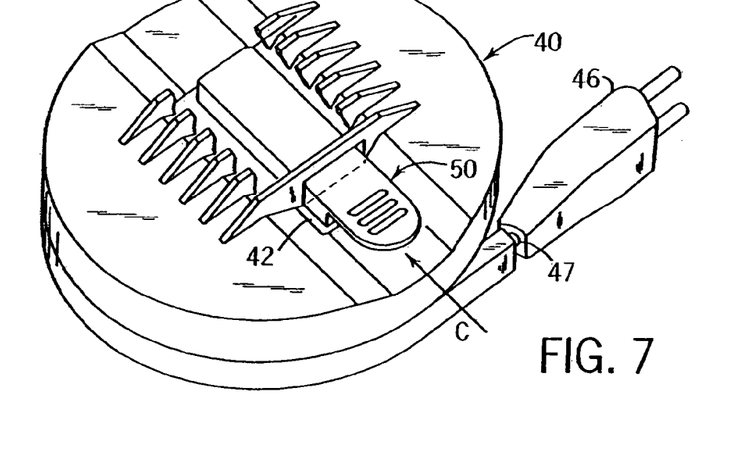
FIG. 7 is a top, perspective view showing a prior art heating device for dispensing volatile materials from a porous mat, with a porous mat of the present invention used therewith.

Turning now to FIG. 7, there is shown a prior art volatile material dispensing device in which a solid porous mat impregnated with a volatile material is heated to release the volatile material. In FIG. 7, there is shown an electrical heater, indicating generally at 40. The heater is the "FUYI VAPE" heater previously described, except that the mat previously used with that heater has been replaced with a mat 50 of the present invention. The heater 40 is an electrical resistance heater, and has a flat, upwardly exposed heating plate 42 on which is placed a mat 50 of the present invention.

An electrical plug 46 supplies electricity to the heating plate 42 by means of an electrical cord 47. The heating plate 42 is energized by inserting the plug 46 into an electrical outlet whereby the heating plate 42 produces heat to heat the mat 50. The volatile material is vaporized by the heat from the heating plate 42. The heating plate may be a ceramic or metal plate.

Figure 8:
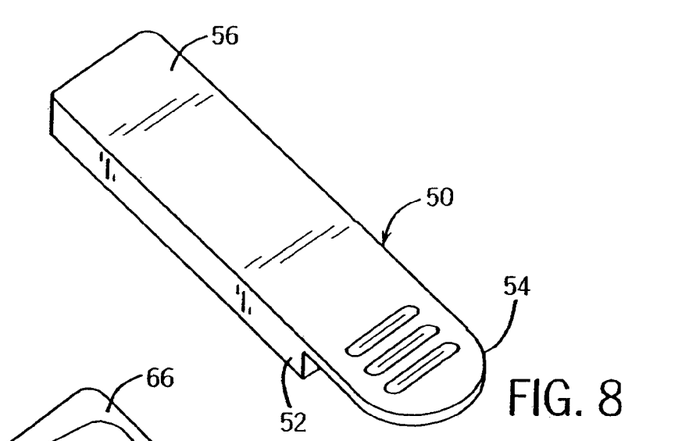
FIG. 8 is an enlarged top perspective view of the FIG. 7 mat.

Referring now to FIG. 8, there is shown one embodiment of a mat 50 according to the invention. The mat 50 is made of a substrate (e.g. ceramic substrate or vitrified sand), which has had wicked into it a polysiloxane and a solvent, with the solvent then being expelled. The substrate then had wicked into it a volatile active such as pyrethrum or pyrethroid.

The mat 50 includes a body 52 and a handle 54 extending outwardly from the body 52. The mat 50 is inserted into the heater 40 by moving the mat 50 in the direction "C" shown in FIG. 7 (sideways in the orientation shown). The mat 50 then rests on the heating plate 42. The heater 40 is then energized by inserting the plug 46 into an electrical outlet whereby the heating plate 42 produces heat to heat the body 52 of the mat 50. The volatile material in the mat 50 is then vaporized by the heat from the heating plate 42 and is released from the surface 56 of the mat 50 thereby entering the surrounding atmosphere.

Figure 9:
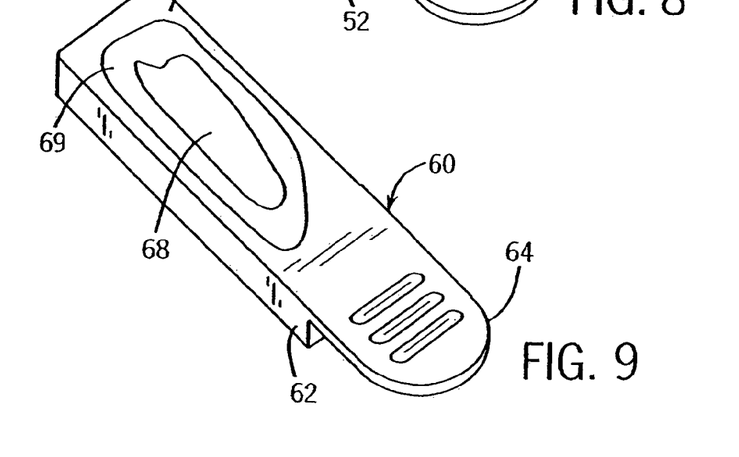
FIG. 9 is a top perspective view of a second porous mat of the present invention.

Referring now to FIG. 9, there is shown another embodiment of a mat 60 according to the invention. The mat 60 is made of a substrate of the present invention and includes a body 62 and a handle 64 extending outwardly from the body 62. The mat 60 differs from the mat 50 in that the mat 60 has a first region 68 impregnated with a first volatile material and a second region 69 impregnated with a second volatile material.

Figure 10:
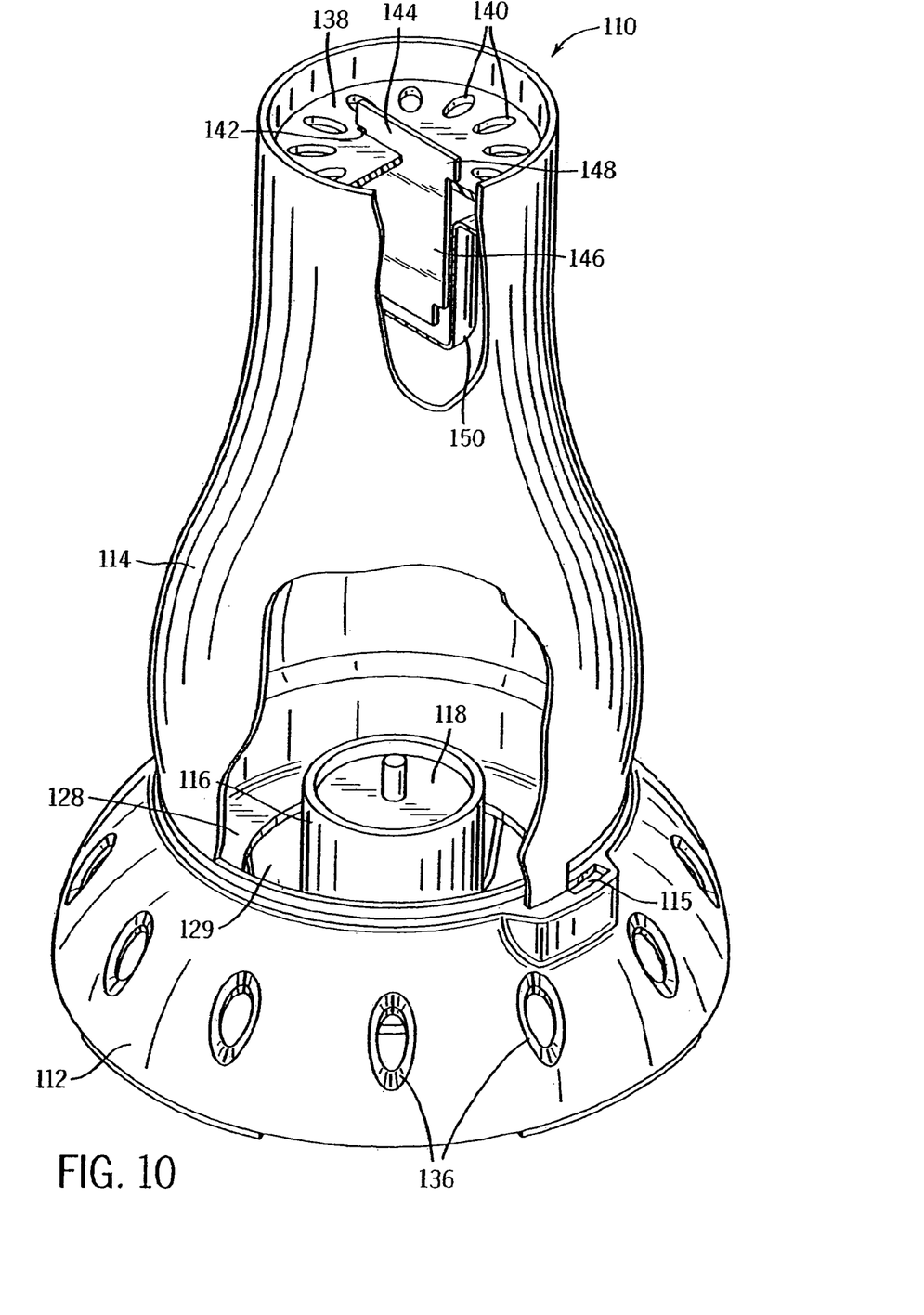
FIG. 10 is a frontal/side perspective view, partially broken away, of another prior art type of heating device, albeit used with another porous mat of the present invention.

In FIG. 10, there is shown a prior art volatile material dispensing device in which a solid porous mat according to the invention is used. The mat is impregnated with a volatile material, and is heated to release the volatile material. The dispensing device 110 has a base 112 that supports a removable chimney 114, the chimney attaching to the base 112 with locking tabs formed on the lower edge of the chimney that mate with locking slots 115 formed in the base 112. The chimney 114 can be made of a heat resistant clear or translucent plastic. The base 112 supports a candle cup 116 positioned centrally within the chimney 114. The candle cup 116 contains a wax candle. The base 112 has a base floor 128 that has a central ventilation opening 129.

A ceiling 138 is positioned within the chimney 114 at its upper end. The ceiling 138 has ceiling vents 140 and an insert slot 142 that communicate between the interior of the chimney 114 and the outside air above the chimney. Hot gases flowing upwardly from the burning candle 118 can escape the chimney 114 through the ceiling vents 140. The insert slot 142 is sized to receive a mat 144 according to the invention. The mat 144 includes a volatile bearing section 146 with laterally extending ears 148. The volatile bearing section 146 of the mat 144 is made small enough to be inserted from above into the insert slot 142, while the ears 148 are made too wide to slip through the insert slot 142.

By this arrangement, the volatile bearing section 146 can be suspended within the chimney 114, with the mat 144 hanging by the ears 148. A baffle strip 150, made of a heat resistant material such as metal, is fastened to the underside of the ceiling 138. The baffle strip 150 protects the downwardly facing edge of the volatile bearing section 146 from the direct impact of the hottest gases rising from the candle. In the dispensing device 110 of FIG. 10, heating is accomplished by the direct exposure of the volatile bearing section 146 to gases from the candle. As the volatile bearing section 146 is heated by the gases, volatile material is released and is carried out of the dispensing device 110 with the escaping hot gases.

Figure 11:
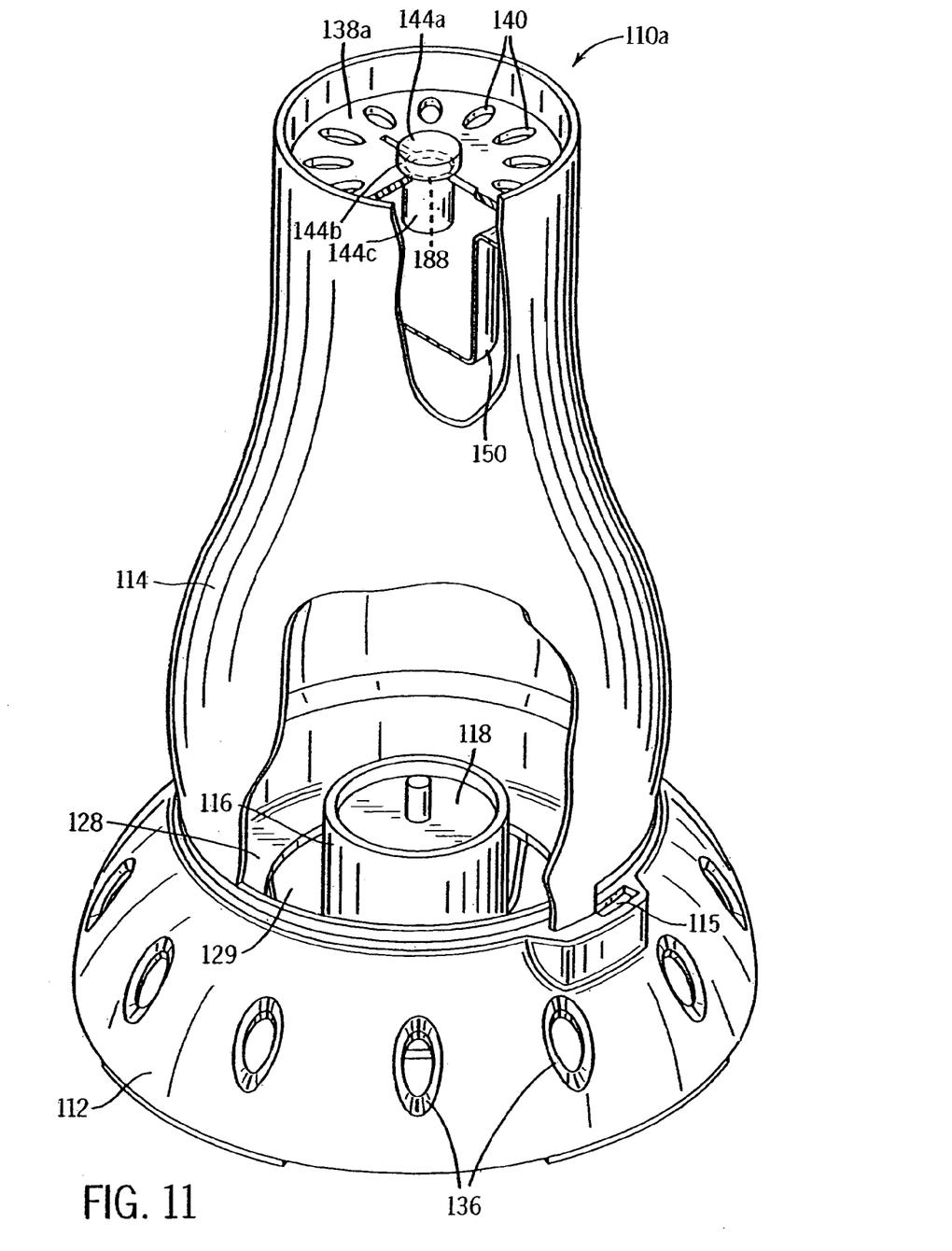
FIG. 11 is a view similar to FIG. 10, but showing a FIG. 10 type of heating device, albeit used with a porous plug of the present invention.

In FIG. 11, there is shown a prior art volatile material dispensing device 110a in which another solid porous structure according to the invention is used. The solid porous structure is impregnated with a volatile material, and is heated to release the volatile material. The volatile material dispensing device 110a of FIG. 11 has the same features as the dispensing device 110 of FIG. 10 except the mat 144 of the dispensing device 110 of FIG. 10 has been replaced by a porous plug 144a in the dispensing device 110a of FIG. 11. The porous plug 144a is installed in a circular hole 188 in the ceiling 138a of the dispensing device 110a.

The porous plug 144a includes a disc shaped head 144b and a cylindrical body 144c that extends downwardly from the head 144b. The body 144c of the plug 144a is made small enough to be inserted from above into the hole 188, while the head 144b is made too wide to slip through the hole 188. By this arrangement, the porous plug 144a can be suspended within the chimney 114, with the body 144c hanging by the head 144b. In the dispensing device 110a of FIG. 11, heating is accomplished by the direct exposure of the porous plug 144a to gases from the candle. As the porous plug 144a is heated by the gases, volatile material is released and is carried out of the dispensing device 110a with the escaping hot gases. The volatile material can be applied to the lower part of the plug 144a so that a user, by handling only the head 144b (the top-most part of the plug 144a) can avoid touching any volatile material.

Heating devices of the above kind typically produce temperatures along the substrate surface of between 100° C. and 180° C., albeit some higher temperatures may be experienced immediately above candle flames, or on some inexpensive heating devices where hot spots arise. Thus, it is preferable to select the polymeric material so as to be stable even in the face of temperatures of 200° C. for 24 hours or more.

The polymeric coating material can be either a homo- or a co-polymer. Examples of polymeric materials that can be used in the present invention include, but are not limited to, polysiloxanes, phenolics (e.g., phenol formaldehyde), polyurethane, and fluorocarbon polymers (e.g., polytetrafluoroethylene and polydifluoroethylene). Examples of polysiloxanes that can be used include but are not limited to polyalkylsiloxanes (e.g. polydialkylsiloxanes such as polydimethylsiloxane and polymethyloctylsiloxane) and polyalkylarylsiloxanes (e.g., polymethylphenylsiloxane). Preferably, the amount of polymeric materials used to coat the porous medium is between about 0.2% to about 4%, and most preferably about 1%, of the porous medium by weight.

Porous media is presented in the form of a wick, a mat, a plug or other dispensing forms, with the media being ceramic, vitrified sand, cellulosic, sawdust, or metal. Ceramics are most preferred, particularly porous ceramics with a pore size of about 15 to about 30 μm.

Examples of the volatile materials that can be dispensed by a substrate of the present invention include but are not limited to pyrethrum, pyrethroid insecticides, carbamate insecticides and organic phosphate insecticides, fragrances such as natural and artificial perfumes (e.g., hydrocarbons, terpenes such as d-limonene and citronellal, alcohols, phenols, aldehydes, ketones, lactones, oxides and esters), deodorants, germicides and repellants. See generally U.S. Pat. Nos. 5,038,394, 4,968,487 and 4,663,315.

To form a substrate of the present invention, one can form or obtain a conventional porous ceramic medium. A suitable polymeric material for coating the interior surface of the conventional substrate can then be dissolved in a solvent. For example, a solution of 14 percent OV-17 (Ohio Valley Specialty Chemical, Marietta, Ohio—polymethylphenylsiloxane) can be dissolved into 86 percent chloroform. Alternatively, the polysiloxane could be between 1 and 15 percent of the mixture. The wick or other substrate can then be placed in the solvent/polymeric material bath and allowed to wick the mixture into the pores and passages of the substrate over a period of several minutes to several hours. For example, we have observed that approximately 1 g of solvent/polymeric material displaced air in a 4 g ceramic wick in about 4 minutes. In other experiments we have used polydimethylsiloxane (OV-101, Ohio Valley Specialty Chemical, Marietta, Ohio).

The wick can then be dried in a vented oven at 50° C. for 1 hour. Alternatively, the wick can be left to dry at room temperature overnight. This expels the chloroform, while leaving the polymeric material coated on the interior surfaces of the pores and passages of the substrate.

The wick can be in the shape shown in FIG. 1B, and be used with the FIG. 1B heater. The volatile material can be, for example, 2.5% Kenya pyrethrum (50% extract), about 93% hydrocarbon solvent (e.g. a mixture of Isopar M and V) (Exxon Mobil, Industrial Chemicals), about 1% of a natural fragrance (e.g. orange oil), optionally about 1% of one or more synthetic insecticides (e.g. prallethrin), and optionally about 2% of an antioxidant such as 2,6-ditertiarybutylphenol. Of course, numerous other formulations for the volatile can be used if desired.

A preferred weight of the ceramic medium for such a wick is around 4 grams. With the chloroform filling the voids in the ceramic medium the typical weight was 5 grams.

An alternative method for forming a substrate of the present invention is to mix a polymeric material with a material for forming a porous medium and then subject the mixture to a process for forming the porous medium. For example, alumina, a material that is sometimes used for making ceramic wicks, can be mixed with polysiloxane beads of a particular diameter for generating a desired pore size. A slurry of alumina and the polysiloxane can then be extruded through a die head to form a "green" wick. The wick can next be "fired," which chemically bonds the alumina and drives off most of the polysiloxane except for a layer of the polysiloxane left behind to coat the pores and passages of the wick.

Polymer-coated wicks formed by impregnating the wicks with a polymer-containing solution were evaluated in comparison to ceramic wicks of similar structure which were not polymer coated. Wick performance was evaluated using a solution of high-boiling isoparaffinic solvent (Isopar-V) containing 1% of a 50% pyrethrum concentrate (pyrethrum—Board of Kenya). As a control, blank Isopar-V was also used with each type of wick.

Performance of the wicks were evaluated by simulating a typical consumer use of such products to control insects. The wick and refill bottles were connected to wall-mounted electric vaporizer units (Baygon, EV-7; Raid Mazda-II, All-out). The vaporizer units were powered by a special circuit that kept the line voltage at 230 volts AC+/−0.2 volts. The room where the test units were installed was maintained at 80° F. with a draft-free condition. Each test unit was cycled 8 hours on and 4 hours off to simulate, albeit accelerate, a daily 8-hour cycle of insect-control. The weight of delivered liquid was assessed by determining the mass of each refill bottle using a precision analytical balance (Mettler) after each 8-hour cycle.

With Isopar-V for only controls, the ceramic untreated wicks delivered steady-state rates of 45+/−3 mg/h and 49+/−4 mg/h, respectively. An uncoated wick with a 0.5% pyrethrum solution declined from a peak of 47 mg/h to nearly zero over time. A wick coated with OV-101 maintained a delivery rate of 47+/−11 mg/h with a 0.5% pyrethrum solution at 350 hours even after the uncoated wick had gone to zero within 100 to 180 hours.

Similar tests were conducted with wicks that were made of vitrified sand. Pyrethrum solutions clogged these wicks easily and caused a substantial decline of the delivery rate of the solutions. Coating the wicks with OV-17 or OV-101 prevented the clogging and the decline of the delivery rate for a period extending after the controls had greatly reduced performance.

Hence, the present invention provides ways of efficiently treating substrates to essentially overcome clogging issues due to a variety of volatiles that are heated. The substrates can be inexpensively and easily manufactured. Further, they provide a reliable and predictable source of volatile delivery.

While the above describes a number of preferred embodiments, it should be appreciated that other embodiments are also within the scope of the invention. For example, the substrates can have other shapes.

Further, the impregnation of the substrate with the polymeric material and/or the volatile can be by dosing, dipping, or other techniques (as distinguished from just wicking). Also, while a number of types of dispensing devices have been disclosed, the exact nature of the heater or blower is not critical.

Thus, the claims which follow should be looked to in order to judge the full scope of the invention.

INDUSTRIAL APPLICABILITY

The present invention provides improved wicks, mats, plugs and the like for dispensing volatiles, particularly for use in dispensing pyrethrum insecticides from electrical heating devices.

We claim:

1. A substrate impregnated with a volatile material comprising pyrethrum to be dispensed from the substrate, the substrate comprising:
   a substrate formed from a medium having pores and passages, the substrate having a pore size of between 15 µm and 30 µm; and having a polymeric material coating interior surfaces of the pores and passages, the substrate having a pore size of between 15 µm and 30 µm; and
   volatile material disposed in the pores;
   wherein the volatile material is more volatile than the polymeric material and the polymeric material inhibits the volatile material from clogging the substrate if the substrate is heated; and
   wherein the polymeric material is selected from the group consisting of polyalkylsiloxanes and polyalkylarylsiloxanes where an alkyl group in the polysiloxane is a $C_1$ to $C_{10}$ alkyl group, phenolic materials, polyurethanes and fluorocarbon polymers; and wherein the polymeric material is selected from the group consisting of polyalkylsiloxanes and polyalkylarylsiloxanes where an alkyl group in the polysiloxane is a Cl to CiO alkyl group, phenolic materials, polyurethanes and fluorocarbon polymers.

2. The substrate of claim 1, wherein the polymeric material is less than 4% of the substrate by weight.

3. A substrate impregnated with a volatile material comprising pyrethrum to be dispensed from the substrate, the substrate comprising:
   a substrate formed from a medium having pores and passages, and having a polymeric material coating interior surfaces of the pores and passages, the substrate having a pore size of between 15 µm and 30 µm; and
   volatile material disposed in the pores;
   wherein the volatile material is more volatile than the polymeric material and the polymeric material inhibits the volatile material from clogging the substrate if the substrate is heated; and
   wherein the polymeric material is selected from the group consisting of polyalkylsiloxanes and polyalkylarylsiloxanes.

4. The substrate of claim 3, wherein an alkyl group in the polysiloxane is a $C_1$ to $C_{10}$ alkyl group.

5. The substrate of claim 4, wherein the polysiloxane is selected from the group consisting of polydimethylsiloxane, polymethylphenylsiloxane, and polymethyloctylsiloxane.

6. The substrate of claim 1, wherein the polysiloxane has a molecular weight of 750 dalton or greater.

7. A substrate impregnated with a volatile material to be dispensed from the substrate, the substrate comprising:
   a substrate formed from a medium having pores and passages, and having a polymeric material coating interior surfaces of the pores and passages; and
   volatile material disposed in the pores;
   wherein the volatile material is more volatile than the polymeric material and the polymeric material inhibits the volatile material from clogging the substrate if the substrate is heated; and wherein the substrate is capable of being heated at 200° C. so as to release at least 90 percent of the volatile material from the substrate.

8. The substrate of claim 7, wherein the substrate is capable of being heated at 200° C. to release at least 95 percent of the volatile material from the substrate.

9. The substrate of claim 1, wherein the substrate is selected from the group consisting of wicks, mats and plugs.

10. The substrate of claim 3, wherein the medium is a ceramic.

11. The substrate of claim 1, wherein the medium is a ceramic.

12. A substrate impregnated with a volatile material to be dispensed from the substrate, the substrate comprising:
 a substrate formed from a medium having pores and passages, and having a polymeric material coating interior surfaces of the pores and passages; and
 volatile material disposed in the pores;
 wherein the volatile material is more volatile than the polymeric material and the polymeric material inhibits the volatile material from clogging the substrate if the substrate is heated; and
 wherein if the substrate is heated to 200° C. for 24 hours the polymeric material therein will not have decomposed as a result thereof.

13. The substrate of claim 3, wherein the volatile material comprises a terpene.

14. The substrate of claim 1, wherein the polymeric material is a phenol formaldehyde.

15. The substrate of claim 1, wherein the polymeric material is selected from the group consisting of polytetrafluoroethylene and polydifluoroethylene.

* * * * *

UNITED STATES PATENT AND TRADEMARK OFFICE
CERTIFICATE OF CORRECTION

| | | |
|---|---|---|
| PATENT NO. | : 7,258,868 B2 | Page 1 of 1 |
| APPLICATION NO. | : 10/758650 | |
| DATED | : August 21, 2007 | |
| INVENTOR(S) | : Kenneth J. Welch, Robert R. Emmrich and Michael J. Aulozzi | |

It is certified that error appears in the above-identified patent and that said Letters Patent is hereby corrected as shown below:

Column 10: Lines 17-18, delete ", the substrate having a pore size of between 15 µm and 30 µm"

Column 10: Lines 28-33, delete "; and wherein the polymeric material is selected from the group consisting of polyalkylsiloxanes and polyalkylarylsiloxanes where an alkyl group in the polysiloxane is a C1 to CiO alkyl group, phenolic materials, polyurethanes and fluorocarbon polymers"

Signed and Sealed this

Twenty-second Day of July, 2008

JON W. DUDAS
*Director of the United States Patent and Trademark Office*